US011142516B2

(12) United States Patent
Peterson et al.

(10) Patent No.: US 11,142,516 B2
(45) Date of Patent: Oct. 12, 2021

(54) PROCESS FOR THE PREPARATION OF AN AMINO-PYRIMIDINE AND INTERMEDIATES THEREOF

(71) Applicant: Cytokinetics, Inc., South San Francisco, CA (US)

(72) Inventors: Matthew Peterson, South San Francisco, CA (US); Kevin Lu, South San Francisco, CA (US); Bradley Morgan, South San Francisco, CA (US); David Morgans, South San Francisco, CA (US); Tohru Fukuyama, Anjo (JP)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 16/958,093

(22) PCT Filed: Dec. 26, 2018

(86) PCT No.: PCT/US2018/067500
§ 371 (c)(1),
(2) Date: Jun. 25, 2020

(87) PCT Pub. No.: WO2019/133605
PCT Pub. Date: Jul. 4, 2019

(65) Prior Publication Data

US 2021/0061786 A1 Mar. 4, 2021

Related U.S. Application Data

(60) Provisional application No. 62/610,302, filed on Dec. 26, 2017.

(51) Int. Cl.
*C07D 401/14* (2006.01)
*C07C 231/02* (2006.01)
*C07C 233/58* (2006.01)
*C07D 213/61* (2006.01)

(52) U.S. Cl.
CPC .......... *C07D 401/14* (2013.01); *C07C 231/02* (2013.01); *C07C 233/58* (2013.01); *C07D 213/61* (2013.01)

(58) Field of Classification Search
CPC .. C07D 401/14; C07D 213/61; C07C 231/02; C07C 233/58
See application file for complete search history.

(56) References Cited

U.S. PATENT DOCUMENTS

| | | | | |
|---|---|---|---|---|
| 8,962,632 B2 * | 2/2015 | Yang | C07D 401/04 | 514/255.05 |
| 9,018,223 B2 * | 4/2015 | Warrington | A61K 9/0019 | 514/275 |
| 9,730,886 B2 * | 8/2017 | Yang | A61P 25/02 | |
| 10,272,030 B2 * | 4/2019 | Yang | C07D 403/10 | |
| 10,765,624 B2 * | 9/2020 | Yang | C07D 513/04 | |
| 2017/0281621 A1 | 10/2017 | Ashcraft | | |
| 2021/0045997 A1 * | 2/2021 | Yang | C07D 403/04 | |

FOREIGN PATENT DOCUMENTS

| | | | |
|---|---|---|---|
| WO | 2011133882 A1 | 10/2011 | |
| WO | 2011133888 A1 | 10/2011 | |
| WO | 2011133920 A1 | 10/2011 | |
| WO | WO-2011133888 A1 * | 10/2011 | A61K 9/0034 |
| WO | 2016039367 A1 | 3/2016 | |

OTHER PUBLICATIONS

International Preliminary Report on Patentability dated Jul. 9, 2020, for Patent Application No. PCT/US2018/067500, filed Dec. 26, 2018, 7 pages.
International Searching Authority and Written Opinion of the International Searching Authority dated May 1, 2019, for International Patent Application No. PCT/US18/67500, filed Dec. 26, 2018, 9 pages.
PubChem-CID-13204884 (Feb. 8, 2007). "3,3-Dimethoxycyclobutane-1-carbonitrile," 12 pages.
Hoz, S. et al. (1986). "Mechanism and Stereochemistry of General Acid Catalyzed Additions to Bicyclobutane," J. Org. Chem. 51:4537-4544.

* cited by examiner

*Primary Examiner* — Alexander R Pagano
(74) *Attorney, Agent, or Firm* — Morrison & Foerster LLP

(57) ABSTRACT

Provided herein is a novel process for the preparation of an amino-pyrimidine and salts thereof. Also provided herein are novel intermediates used in this process and their preparation.

29 Claims, No Drawings

PROCESS FOR THE PREPARATION OF AN AMINO-PYRIMIDINE AND INTERMEDIATES THEREOF

CROSS REFERENCE TO RELATED APPLICATIONS

This application is a national stage application under 35 U.S.C. § 371 of International Application No. PCT/US2018/067500, filed internationally on Dec. 26, 2018, which claims benefit of U.S. Provisional Application No. 62/610,302, filed on Dec. 26, 2017, the disclosures of which are herein incorporated by reference in their entirety.

FIELD

Provided herein is a novel process for the preparation of an amino-pyrimidine and salts thereof. Also provided herein are novel intermediates used in this process and their preparation.

BACKGROUND

The cytoskeleton of skeletal and cardiac muscle cells is unique compared to that of all other cells. It consists of a nearly crystalline array of closely packed cytoskeletal proteins called the sarcomere. The sarcomere is elegantly organized as an interdigitating array of thin and thick filaments. The thick filaments are composed of myosin, the motor protein responsible for transducing the chemical energy of ATP hydrolysis into force and directed movement. The thin filaments are composed of actin monomers arranged in a helical array. There are four regulatory proteins bound to the actin filaments, which allows the contraction to be modulated by calcium ions. An influx of intracellular calcium initiates muscle contraction; thick and thin filaments slide past each other driven by repetitive interactions of the myosin motor domains with the thin actin filaments.

Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II forms homo-dimers resulting in two globular head domains linked together by a long alpha-helical coiled-coiled tail to form the core of the sarcomere's thick filament. The globular heads have a catalytic domain where the actin binding and ATPase functions of myosin take place. Once bound to an actin filament, the release of phosphate (cf. ADP-Pi to ADP) signals a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound. Un-binding of the globular head from the actin filament ($Ca^{2+}$ regulated) coupled with return of the catalytic domain and light chain to their starting conformation/orientation completes the catalytic cycle, responsible for intracellular movement and muscle contraction.

Tropomyosin and troponin mediate the calcium effect on the interaction on actin and myosin. The troponin complex is comprised of three polypeptide chains: troponin C, which binds calcium ions; troponin I, which binds to actin; and troponin T, which binds to tropomyosin. The skeletal troponin-tropomyosin complex regulates the myosin binding sites extending over several actin units at once.

Troponin, a complex of the three polypeptides described above, is an accessory protein that is closely associated with actin filaments in vertebrate muscle. The troponin complex acts in conjunction with the muscle form of tropomyosin to mediate the $Ca^{2+}$ dependency of myosin ATPase activity and thereby regulate muscle contraction. The troponin polypeptides T, I, and C, are named for their tropomyosin binding, inhibitory, and calcium binding activities, respectively. Troponin T binds to tropomyosin and is believed to be responsible for positioning the troponin complex on the muscle thin filament. Troponin I binds to actin, and the complex formed by troponins I and T, and tropomyosin inhibits the interaction of actin and myosin. Skeletal troponin C is capable of binding up to four calcium molecules. Studies suggest that when the level of calcium in the muscle is raised, troponin C exposes a binding site for troponin I, recruiting it away from actin. This causes the tropomyosin molecule to shift its position as well, thereby exposing the myosin binding sites on actin and stimulating myosin ATPase activity.

U.S. Pat. No. 8,962,632 discloses 1-(2-4((trans)-3-fluoro-1-(3-fluoropyridin-2-yl)cyclobutyl)methyl)amino)pyrimidin-5-yl)-1H-pyrrole-3-carboxamide, a next-generation fast skeletal muscle troponin activator (FSTA) as a potential treatment for people living with debilitating diseases and conditions associated with neuromuscular or non-neuromuscular dysfunction, muscular weakness, and/or muscle fatigue.

There is a need for improved methods for preparing such compound with low cost and high overall yield and purity.

BRIEF SUMMARY

In one aspect, provided herein is method of preparing a compound of Formula (1):

(1)

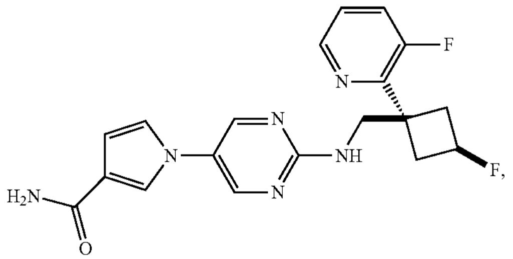

or a salt thereof, comprising:

(i) reacting a compound of Formula (1A):

(1A)

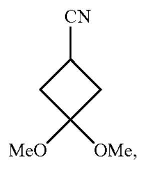

with 2-chloro-3-fluoropyridine to form a compound of Formula (1B):

(1B)

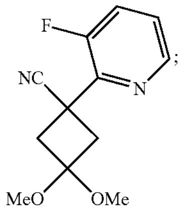

(ii) reacting the compound of Formula (1B) with an aqueous acid to form a compound of Formula (1C):

(1C)

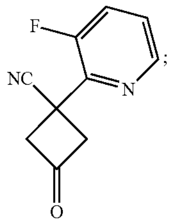

and (iii) converting the compound of Formula (1C) to the compound of Formula (1) or a salt thereof.

In some embodiments, the method further comprises obtaining the compound of Formula (1A) by reacting a compound of Formula (2A):

(2A)

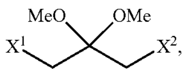

wherein $X^1$ and $X^2$ are each independently a leaving group, with a compound of Formula (2B):

(2B)

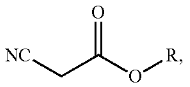

where R is optionally substituted alkyl, optionally substituted alkenyl, optionally substituted alkynyl, optionally substituted cycloalkyl, optionally substituted heterocycloalkyl, optionally substituted aryl, or optionally substituted heteroaryl, to form the compound of Formula (1A). In some embodiments, $X^1$ and $X^2$ are independently halo, triflate, tosylate, mesylate, or acetoxy. In some embodiments, $X^1$ and $X^2$ are independently halo.

In some embodiments, the method further comprises obtaining the compound of Formula (1A) by reacting 1,3-dibromo-2,2-dimethoxypropane with tert-butyl 2-cyanoacetate to form the compound of Formula (1A).

In some embodiments, the reaction of the 1,3-dibromo-2,2-dimethoxypropane with the tert-butyl 2-cyanoacetate is performed in the presence of a base.

In some embodiments, the base is potassium tert-butoxide.

In some embodiments, the method further comprises obtaining the compound of Formula (1A) by converting a compound of Formula (1D):

(1D)

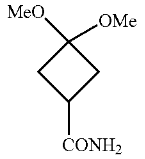

to the compound of Formula (1A).

In some embodiments, the method further comprises obtaining the compound of Formula (1D) by converting a compound of Formula (1E):

(1E)

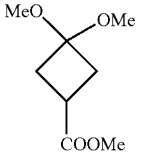

to the compound of Formula (1D).

In some embodiments, the method further comprises obtaining the compound of Formula (1E) by converting a compound of Formula (1F):

(1F)

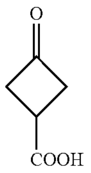

to the compound of Formula (1E).

In some embodiments, step (i) is performed in the presence of a base.

In some embodiments, the base is sodium bis(trimethylsilyl)amide.

In some embodiments, the aqueous acid of step (ii) is aqueous hydrochloric acid.

In some embodiments, step (iii) comprises converting the compound of Formula (1C) to a compound of Formula (1G):

(1G)

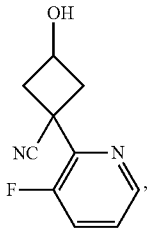

and converting the compound of Formula (1G) to the compound of Formula (1) or a salt thereof.

In some embodiments, step (iii) further comprises converting the compound of Formula (1G) to a compound of Formula (1H):

(1H)

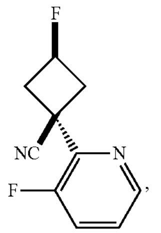

and converting the compound of Formula (1H) to the compound of Formula (1) or a salt thereof.

In some embodiments, step (iii) further comprises converting the compound of Formula (1H) to a compound of Formula (1I)

(1I)

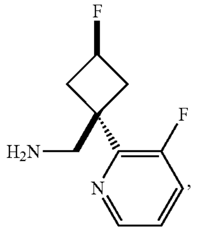

and converting the compound of Formula (1I) to the compound of Formula (1) or a salt thereof.

In some embodiments, step (iii) further comprises reacting the compound of Formula (1I) with

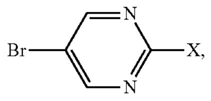

wherein X is chloro or fluoro, to form a compound of Formula (1J):

(1J)

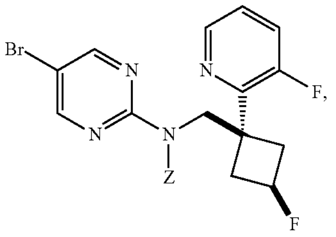

wherein Z is a protecting group or hydrogen, and converting the compound of Formula (1J) to the compound of Formula (1) or a salt thereof.

In some embodiments, step (iii) further comprises reacting the compound of Formula (1J) with

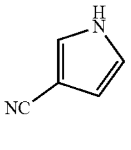

to form a compound of Formula (1K):

(1K)

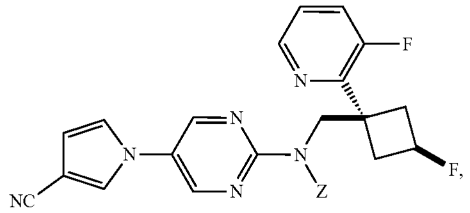

wherein Z is a protecting group or hydrogen, and converting the compound of Formula (1K) to the compound of Formula (1) or a salt thereof.

In some embodiments, Z is Boc. In some embodiments, Z is hydrogen.

In some embodiments, step (iii) comprises isolating the compound of Formula (1) or a salt thereof.

In another aspect, provided herein is a compound of Formula (1B):

(1B)

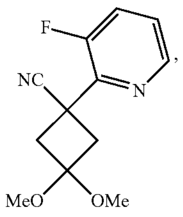

or a salt thereof.

In some embodiments, provided is a method of preparing a compound of Formula (1B):

(1B)

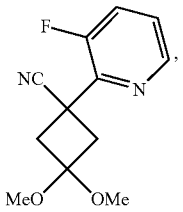

or a salt thereof, comprising:

reacting a compound of Formula (1A):

(1A)

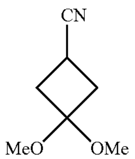

with 2-chloro-3-fluoropyridine to form the compound of Formula (1B).

In some embodiments, the method further comprises obtaining the compound of Formula (1A) by reacting 1,3-dibromo-2,2-dimethoxypropane with tert-butyl 2-cyanoacetate to form the compound of Formula (1A).

In some embodiments, the reaction of the 1,3-dibromo-2,2-dimethoxypropane with the tert-butyl 2-cyanoacetate is performed in the presence of a base.

In some embodiments, the base is potassium tert-butoxide.

In some embodiments, the method further comprises obtaining the compound of Formula (1A) by converting a compound of Formula (1D):

(1D)

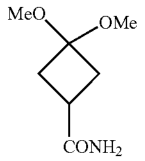

to the compound of Formula (1A).

In some embodiments, the method further comprises obtaining the compound of Formula (1D) by converting a compound of Formula (1E):

(1E)

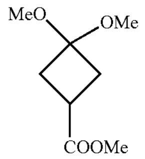

to the compound of Formula (1D).

In some embodiments, the method further comprises obtaining the compound of Formula (1E) by converting a compound of Formula (1F):

(1F)

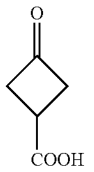

to the compound of Formula (1E).

In some embodiments, the reaction of the compound of Formula (1A) with the 2-chloro-3-fluoropyridine is performed in the presence of a base.

In some embodiments, the base is sodium bis(trimethylsilyl)amide.

In another aspect, provided herein is a compound of Formula (1D):

(1D)

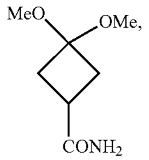

or a salt thereof.

In some embodiments, provided herein is a method of preparing a compound of Formula (1D):

(1D)

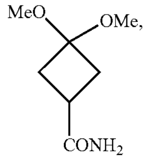

or a salt thereof, comprising converting a compound of Formula (1E):

(1E)

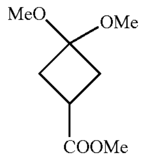

to the compound of Formula (1D) or a salt thereof.

In some embodiments, the method further comprises obtaining the compound of Formula (1E) by converting a compound of Formula (1F):

(1F)

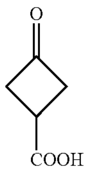

to the compound of Formula (1E).

DETAILED DESCRIPTION

Definitions

As used herein and unless otherwise stated or implied by context, terms that are used herein have the meanings defined below. Unless otherwise contraindicated or implied, e.g., by including mutually exclusive elements or options, in those definitions and throughout this specification, the terms "a" and "an" mean one or more and the term "or" means and/or where permitted by context. Thus, as used in the specification and the appended claims, the singular forms "a," "an," and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Embodiments also specifically include those compounds, compositions, compositions or methods that are, or that consist of, or that consist essentially of those specified components, elements or steps. The term "comprised of" is used interchangeably with the term "comprising" and are stated as equivalent terms. For example, disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist of" a component or step are closed and they would not include or read on those compositions or methods having appreciable amounts of an additional component(s) or an additional step(s). Furthermore, the term "consisting essentially of" admits for the inclusion of unrecited elements that have no material effect on the functionality of the disclosed compositions, devices, articles of manufacture or methods for its intended purpose as further defined herein. The section headings used herein are for organizational purposes only and are not to be construed as limiting the subject matter described.

"About" as used herein when used in connection with a numeric value or range of values provided to describe a particular property of a compound or composition indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicates that the numeric value or range of values can vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, or 0.01% of the recited value or range of values, such as by 10% to 0.5% or by 5% to 1%, while still describing the particular property.

"Alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C═C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-1-en-2-yl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkynyl" as used herein refers to an unsaturated linear or branched univalent hydrocarbon chain or combination thereof, having at least one site of acetylenic unsaturation (i.e., having at least one moiety of the formula CC) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Cycloalkyl" as used herein refers to a $C_3$-$C_{10}$ saturated or unsaturated non-aromatic hydrocarbon ring group. The cycloalkyl may have a bridge. Examples of the cycloalkyl include, but are not limited to, cyclopropyl, cyclobutyl, cyclopentyl, cyclohexyl, cyclohexenyl, cycloheptyl, cyclooctyl.

"Aryl" as used herein refers to a $C_6$-$C_{12}$ unsaturated aromatic hydrocarbon ring group. Aryl may be monocyclic or polycyclic (e.g., bicyclic, tricyclic). Ary may be fused to rings (e.g., from 1 to 3 rings), including, but are not limited to, aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

"Heteroaryl" as used herein refers to unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may be fused to rings (e.g., from 1 to 3 rings), including, but are not limited to, aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

"Heterocycle", "heterocyclyl" or "heterocycloalkyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

"Halo" refers to fluoro, chloro, bromo or iodo. In another embodiment, halo is fluoro. In another embodiment, halo is bromo.

"Heteroalkyl" refers to alkyl which is substituted with alkoxy group. Examples of heteroalkyl group include, but are not limited to, methoxymethyl, ethoxymethyl, and the like.

"Oxo" refers to the moiety ═O.

"Substituted" as used herein means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alkylsulfonyl, sulfonic acid, alkylsulfonyl, thiocyanate, thiol, thione, or combinations thereof.

"Optionally substituted" as used herein means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents. It is understood that where a chemical moiety here is "optionally substituted," the disclosure includes embodiments in which the moiety is substituted and embodiments in which the moiety is unsubstituted.

"Protecting group" as used herein, unless otherwise stated or implied by context, refers to a moiety that prevents or substantially reduces the ability of the atom or functional group to which it is linked from participating in unwanted reactions. Typical protecting groups for atoms or functional groups are given in Greene (2014), "Protective groups in organic synthesis, $5^{th}$ ed.", Wiley Interscience. Protecting groups for heteroatoms such as oxygen, sulfur and nitrogen are sometime used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —$OR^{PR}$, wherein $R^{PR}$ is a protecting group for hydroxyl, wherein hydroxyl is in some embodiments protected as an ester (e.g., acetate, propionate or benzoate). Other protecting groups for hydroxyl avoid its interference with the nucleophilicity of organometallic reagents or other highly basic reagents, for which purpose hydroxyl is in some embodiments protected as an ether, including without limitation alkyl or heterocyclyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TB S/TBDMS), triisopropylsilyl (TIPS) and [2-(trimethylsilyl)ethoxy]-methylsilyl (SEM)). Nitrogen protecting groups include those for primary or secondary amines as in —$NHR^{PR}$ or —$N(R^{PR})_2$, wherein at least one of $R^{PR}$ is a nitrogen atom protecting group or both $R^{PR}$ together define a nitrogen atom protecting group.

A protecting group is a suitable for protecting when it is capable of preventing or substantially avoiding unwanted side-reactions and/or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. In some aspects, suitable protecting groups are those previously described for protecting functional groups. For example, a suitable protecting group for the basic nitrogen atom of an acyclic or cyclic basic group is an acid-labile carbamate protecting group such as t-butyloxycarbonyl (Boc).

Each compound disclosed herein may be in a salt form. The compound may contain at least one amino group, and accordingly acid addition salts can be formed with this amino group. Exemplary salts include, without limitation, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

A salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a salt can have one or more charged atoms and/or one or more counterions.

"Pharmaceutically acceptable salt" refers to salts which possess toxicity profiles within a range that affords utility in pharmaceutical applications. In some embodiments, a pharmaceutically acceptable salt is selected from those described in P. H. Stahl and C. G. Wermuth, editors, *Handbook of Pharmaceutical Salts: Properties, Selection and Use*, Weinheim/Zürich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

Methods

In one aspect, provided herein is method of preparing a compound of Formula (1):

(1)

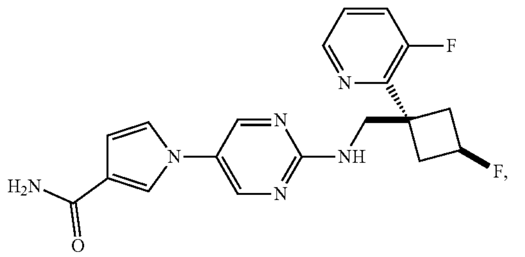

or a salt thereof, comprising:

(i) reacting a compound of Formula (1A):

(1A)

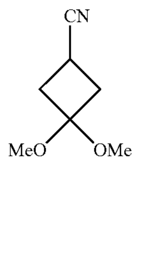

with 2-chloro-3-fluoropyridine to form a compound of Formula (1B):

(1B)

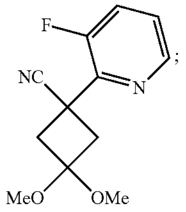

(ii) reacting the compound of Formula (1B) with an aqueous acid to form a compound of Formula (1C):

(1C)

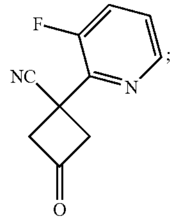

and (iii) converting the compound of Formula (1C) to the compound of Formula (1) or a salt thereof.

In some embodiments, step (i) is performed in the presence of a base. In some embodiments, the base is an inorganic base. Examples of inorganic bases include, without limitation, potassium carbonate, sodium carbonate, cesium carbonate, potassium bicarbonate, sodium bicarbonate, sodium hydroxide, potassium hydroxide, magnesium hydroxide, lithium hydroxide, sodium tert-butoxide, potassium carbonate, sodium bis(trimethylsilyl)amide and the like. In some embodiments, the base is an organic base. Examples of organic bases include, without limitation, N,N-Diisopropylethylamine, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine and N-methylglucamine. In some embodiments, the base is sodium bis(trimethylsilyl)amide.

In some embodiments, step (i) is performed in an organic solvent. Examples of organic solvents includes, without limitations, hexane, pentane, cyclopentane, cyclohexane, benzene, toluene, 1,4-dioxane, dichloromethane (DCM), chloroform, ethyl acetate, tetrahydrofuran (THF), dichloromethane, acetone, acetonitrile (MeCN), dimethylformamide (DMF), dimethyl sulfoxide (DMSO), 1,3-dimethyl-2-imidazolidinone (DMI), acetic acid, n-butanol, isopropanol, n-propanol, ethanol, and methanol and the like. In some embodiments, the organic solvent is any compatible mixture of organic solvent such as those given as examples herein. In some embodiments, the organic solvent is free of water. In some embodiments, the organic solvent comprises water. In some embodiments, step (i) is performed in toluene. It is understood that each description of the organic solvent may be combined with each description of the base the same as if each and every combination were specifically and individually listed. For example, in some embodiments, step (i) is performed in toluene in the presence of sodium bis(trimethylsilyl)amide.

In some embodiments, step (i) is performed at a temperature of about 100° C., about 90° C., about 80° C., about 70° C., about 60° C., about 50° C., about 40° C., about 30° C., about 20° C., about 10° C., about 0° C., about −10° C., about −20° C., about −30° C., about −40° C., about −50° C., or about −60° C. In some embodiments, step (i) is performed at a temperature of less than about 100° C., about 90° C., about 80° C., about 70° C., about 60° C., about 50° C., about 40° C., about 30° C., about 20° C., about 10° C., about 0° C., about −10° C., about −20° C., about −30° C., about −40° C., about −50° C., or about −60° C. In some embodiments, step (i) is performed at a temperature of at least about 100° C., about 90° C., about 80° C., about 70° C., about 60° C., about 50° C., about 40° C., about 30° C., about 20° C., about 10° C., about 0° C., about −10° C., about −20° C., about −30° C., about −40° C., about −50° C., or about −60° C. In some embodiments, step (i) is performed at a temperature of between about 10° C. and about −60° C., between about 0° C. and about −60° C., between about −10° C. and about −60° C., between about 10° C. and about −40° C., between about 0° C. and about −40° C., between about −10° C. and about −40° C., between about 10° C. and about −30° C., between about 0° C. and about −30° C., or between about −10° C. and about −30° C. In some embodiments, step (i) is performed at a temperature of about −20° C. It is understood that each description of the temperature may be combined with each description of the base and/or the organic solvent the same as if each and every combination were specifically and individually listed. For example, in some embodiments, step (i) is performed in toluene in the presence of sodium bis(trimethylsilyl)amide at a temperature of about −20° C.

In some embodiments, the aqueous acid of step (ii) is an inorganic acid. Examples of inorganic acids include, without limitation, hydrochloric acid, hydrobromic acid, sulfuric acid, sulfamic acid, nitric acid, boric acid, phosphoric acid, and the like. In some embodiments, the aqueous acid of step (ii) is an organic acid. Examples of organic acids include acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, pyranosidyl acid, and the like. In some embodiments, the aqueous acid is any compatible mixture of acids such as those given as examples herein. In some embodiments, the aqueous acid of step (ii) is hydrochloric acid.

In some embodiments, step (ii) is performed at a temperature of about 100° C., about 90° C., about 80° C., about 70° C., about 60° C., about 50° C., about 40° C., about 30° C., about 20° C., about 10° C., or about 0° C. In some embodiments, step (i) is performed at a temperature of less than about 100° C., about 90° C., about 80° C., about 70° C., about 60° C., about 50° C., about 40° C., about 30° C., about 20° C., or about 10° C. In some embodiments, step (i) is performed at a temperature of at least about 90° C., about 80° C., about 70° C., about 60° C., about 50° C., about 40° C., about 30° C., about 20° C., about 10° C., or about 0° C. In some embodiments, step (ii) is performed at a temperature of about 50° C. It is understood that each description of the temperature may be combined with each description of the aqueous acid the same as if each and every combination were specifically and individually listed. For example, in some embodiments, step (ii) is performed in the presence of hydrochloric acid at a temperature of about 50° C.

In some embodiments, step (iii) comprises converting the compound of Formula (1C) to a compound of Formula (1G):

(1G)

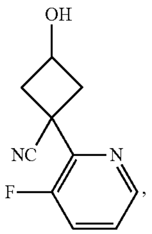

and converting the compound of Formula (1G) to the compound of Formula (1) or a salt thereof. In some embodiments, the conversion of the compound of Formula (1C) to the compound of Formula (1G) is conducted in a mixture of DCM and methanol. In some embodiments, the conversion of the compound of Formula (1C) to the compound of Formula (1G) is conducted in the presence of $NaBH_4$. In some embodiments, the conversion of the compound of Formula (1C) to the compound of Formula (1G) is conducted at a temperature of about −78° C.

In some embodiments, step (iii) further comprises converting the compound of Formula (1G) to a compound of Formula (1H):

(1H)

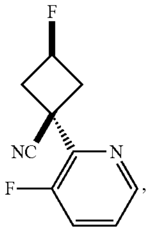

and converting the compound of Formula (1H) to the compound of Formula (1) or a salt thereof. In some embodiments, the conversion of the compound of Formula (1G) to the compound of Formula (1H) is conducted in DCM. In some embodiments, the conversion of the compound of Formula (1G) to the compound of Formula (1H) is conducted in the presence of diethylaminosulfur trifluoride (DAST). In some embodiments, the conversion of the compound of Formula (1G) to the compound of Formula (1H) is conducted at a temperature between about 0° C. and about 10° C.

In some embodiments, step (iii) further comprises converting the compound of Formula (1H) to a compound of Formula (1I)

(1I)

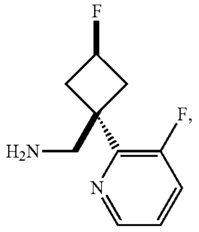

and converting the compound of Formula (1I) to the compound of Formula (1) or a salt thereof. In some embodiments, the conversion of the compound of Formula (1H) to the compound of Formula (1I) is conducted in methanol. In some embodiments, the conversion of the compound of Formula (1H) to the compound of Formula (1I) is conducted in the presence of Raney nickel. In some embodiments, the conversion of the compound of Formula (1H) to the compound of Formula (1I) is conducted in the presence of ammonia.

In some embodiments, step (iii) further comprises reacting the compound of

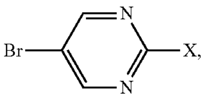

Formula (1I) with wherein X is chloro or fluoro, to form a compound of Formula (1J):

(1J)

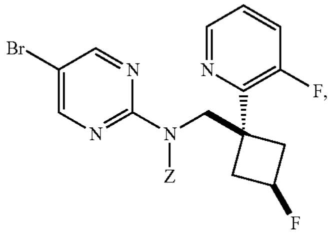

wherein Z is a protecting group or hydrogen, and converting the compound of Formula (1J) to the compound of Formula (1) or a salt thereof. In some embodiments, X is chloro. In some embodiments, X is fluoro. In some embodiments, Z is Boc. In some embodiments, Z is hydrogen. In some embodiments, the conversion of the compound of Formula (1I) to the compound of Formula (1J) is conducted in the presence of NMP. In some embodiments, the conversion of the compound of Formula (1I) to the compound of Formula (1J) is conducted in the presence of DIPEA. In some embodiments, the conversion of the compound of Formula (1I) to the compound of Formula (1J) is conducted in the presence of DMAP. In some embodiments, the conversion of the compound of Formula (1I) to the compound of Formula (1J) is conducted in the presence of $Boc_2O$. In some embodiments, the conversion of the compound of Formula (1I) to the compound of Formula (1J) is conducted in the presence of THF. In some embodiments, the conversion of the compound of Formula (1I) to the compound of Formula (1J) is conducted at a temperature of about 60° C.

In some embodiments, step (iii) further comprises reacting the compound of Formula (1J) with

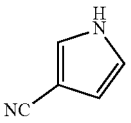

to form a compound of Formula (1K):

(1K)

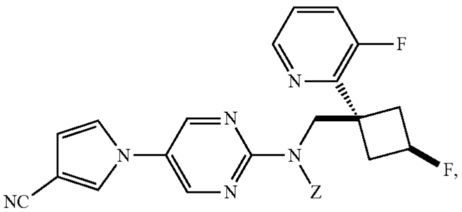

wherein Z is a protecting group or hydrogen, and converting the compound of Formula (1K) to the compound of Formula (1) or a salt thereof. In some embodiments, Z is Boc. In some embodiments, Z is hydrogen. In some embodiments, the reaction of the compound of Formula (1J) with

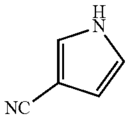

is conducted in toluene. In some embodiments, the reaction of the compound of Formula (1J) with

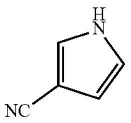

is conducted in the presence of copper iodide. In some embodiments, the reaction of the compound of Formula (1J) with

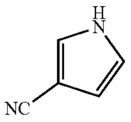

is conducted in the presence of potassium phosphate. In some embodiments, the reaction of the compound of Formula (1J) with

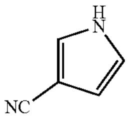

is conducted in the presence of trans-N,N'-dimethylcyclohexane-1,2-diamine. In some embodiments, the reaction of the compound of Formula (1J) with

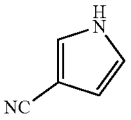

is conducted at a temperature of about 100° C.

In some embodiments, step (iii) comprises isolating the compound of Formula (1) or a salt thereof.

In some embodiments, the method of preparing the compound of Formula (1) or a salt thereof further comprises obtaining the compound of Formula (1A) by reacting a compound of Formula (2A):

(2A)

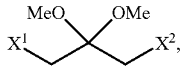

wherein $X^1$ and $X^2$ are each independently a leaving group, with a compound of Formula (2B):

(2B)

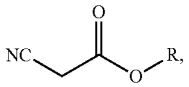

where R is optionally substituted alkyl, optionally substituted alkenyl, optionally substituted alkynyl, optionally substituted cycloalkyl, optionally substituted heterocycloalkyl, optionally substituted aryl, or optionally substituted heteroaryl, to form the compound of Formula (1A).

In some embodiments, $X^1$ and $X^2$ are independently halo, triflate, tosylate, mesylate, or acetoxy. In some embodiments, $X^1$ and $X^2$ are independently halo. In some embodiments, $X^1$ and $X^2$ are both fluoro. In some embodiments, $X^1$ and $X^2$ are both chloro. In some embodiments, $X^1$ and $X^2$ are both bromo. In some embodiments, $X^1$ and $X^2$ are both iodo. In some embodiments, $X^1$ and $X^2$ are different. In some embodiments $X^1$ is fluoro. In some embodiments, $X^1$ is chloro. In some embodiments, $X^1$ is bromo. In some embodiments, $X^1$ is iodo. In some embodiments $X^2$ is fluoro. In some embodiments, $X^2$ is chloro. In some embodiments, $X^2$ is bromo. In some embodiments, $X^2$ is iodo. It is understood that each description of $X^1$ may be combined with each description of $X^2$ as if each and every combination were specifically and individually listed.

In some embodiments, R is optionally substituted alkyl. In some embodiments, R is unsubstituted alkyl. In some embodiments, R is optionally substituted linear alkyl. In some embodiments, R is optionally substituted branched alkyl. In some embodiments, R is optionally substituted $C_1$-$C_6$ alkyl. In some embodiments, R is optionally substituted linear $C_1$-$C_6$ alkyl. In some embodiments, R is optionally substituted branched $C_1$-$C_6$ alkyl. In some embodiments, R is tert-butyl.

It is understood that each description of $X^1$ and/or $X^2$ may be combined with each description of R the same as if each and every combination were specifically and individually listed. In some embodiments, the compound of Formula (2A) is 1,3-dibromo-2,2-dimethoxypropane, and the compound of Formula (2B) is tert-butyl 2-cyanoacetate.

In some embodiments, the reaction of the compound of Formula (2A) (e.g., 1,3-dibromo-2,2-dimethoxypropane)

with the compound of Formula (2B) (e.g., tert-butyl 2-cyanoacetate) is performed in the presence of a base. In some embodiments, the base is an inorganic base. Examples of inorganic bases include, without limitation, potassium carbonate, sodium carbonate, cesium carbonate, potassium bicarbonate, sodium bicarbonate, sodium hydroxide, potassium hydroxide, magnesium hydroxide, lithium hydroxide, sodium tert-butoxide, potassium carbonate, sodium bis(trimethylsilyl)amide and the like. In some embodiments, the base is an organic base. Examples of organic bases include, without limitation, N,N-Diisopropylethylamine, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine and N-methylglucamine. In some embodiments, the base is any compatible mixture of bases such as those given as examples herein. In some embodiments, the base is potassium tert-butoxide. It is understood that each description of the base may be combined with each description of $X^1$, $X^2$, and/or R the same as if each and every combination were specifically and individually listed. For example, in some embodiments, the compound of Formula (2A) is 1,3-dibromo-2,2-dimethoxypropane; the compound of Formula (2B) is tert-butyl 2-cyanoacetate; and the base is potassium tert-butoxide.

In some embodiments, the reaction of the compound of Formula (2A) (e.g., 1,3-dibromo-2,2-dimethoxypropane) with the compound of Formula (2B) (e.g., tert-butyl 2-cyanoacetate) is performed in an organic solvent. Examples of organic solvents includes, without limitations, hexane, pentane, cyclopentane, cyclohexane, benzene, toluene, 1,4-dioxane, chloroform, ethyl acetate, tetrahydrofuran (THF), dichloromethane, acetone, dimethylacetamide (DMAc), acetonitrile (MeCN), dimethylformamide (DMF), dimethyl sulfoxide (DMSO), 1,3-dimethyl-2-imidazolidinone (DMI), N-methylpyrrolidone (NMP), acetic acid, n-butanol, isopropanol, n-propanol, ethanol, and methanol and the like. In some embodiments, the organic solvent is any compatible mixture of organic solvent such as those given as examples herein. In some embodiments, the organic solvent is free of water. In some embodiments, the organic solvent comprises water. In some embodiments, the organic solvent is selected from the group consisting of DMI, DMAc, DMSO, and NMP. In some embodiments, the organic solvent is DMI. In some embodiments, the organic solvent is DMAc. In some embodiments, the organic solvent is DMSO. In some embodiments, the organic solvent is NMP. It is understood that each description of the organic solvent may be combined with each description of $X^1$, $X^2$, R, and/or the base the same as if each and every combination were specifically and individually listed. For example, in some embodiments, the compound of Formula (2A) is 1,3-dibromo-2,2-dimethoxypropane; the compound of Formula (2B) is tert-butyl 2-cyanoacetate; the base is potassium tert-butoxide; and the organic solvent is DMI.

In some embodiments, the reaction of the compound of Formula (2A) (e.g., 1,3-dibromo-2,2-dimethoxypropane) with the compound of Formula (2B) (e.g., tert-butyl 2-cyanoacetate) is performed at a temperature of about 200° C., about 190° C., about 180° C., about 170° C., about 160° C., about 150° C., about 140° C., about 130° C., about 120° C., about 110° C., about 100° C., about 90° C., about 80° C., about 70° C., about 60° C., about 50° C., about 40° C., about 30° C., about 20° C., about 10° C., about 0° C., about −10° C., about −20° C., or about −30° C. In some embodiments, the reaction of the compound of Formula (2A) (e.g., 1,3-dibromo-2,2-dimethoxypropane) with the compound of Formula (2B) (e.g., tert-butyl 2-cyanoacetate) is performed at a temperature of less than about 200° C., about 190° C., about 180° C., about 170° C., about 160° C., about 150° C., about 140° C., about 130° C., about 120° C., about 110° C., about 100° C., about 90° C., about 80° C., about 70° C., about 60° C., about 50° C., about 40° C., about 30° C., about 20° C., about 10° C., about 0° C., about −10° C., about −20° C., or about −30° C. In some embodiments, the reaction of the compound of Formula (2A) (e.g., 1,3-dibromo-2,2-dimethoxypropane) with the compound of Formula (2B) (e.g., tert-butyl 2-cyanoacetate) is performed at a temperature of at least about 200° C., about 190° C., about 180° C., about 170° C., about 160° C., about 150° C., about 140° C., about 130° C., about 120° C., about 110° C., about 100° C., about 90° C., about 80° C., about 70° C., about 60° C., about 50° C., about 40° C., about 30° C., about 20° C., about 10° C., about 0° C., about −10° C., about −20° C., or about −30° C. In some embodiments, the reaction of the compound of Formula (2A) (e.g., 1,3-dibromo-2,2-dimethoxypropane) with the compound of Formula (2B) (e.g., tert-butyl 2-cyanoacetate) is performed at a temperature of between about 200° C. and about 100° C., between about 200° C. and about 110° C., between about 200° C. and about 120° C., between about 200° C. and about 130° C., between about 200° C. and about 140° C., between about 180° C. and about 100° C., between about 180° C. and about 110° C., between about 180° C. and about 120° C., between about 180° C. and about 130° C., between about 180° C. and about 140° C., between about 160° C. and about 100° C., between about 160° C. and about 110° C., between about 160° C. and about 120° C., between about 190° C. and about 130° C., or between about 160° C. and about 140° C. In some embodiments, the reaction of the compound of Formula (2A) (e.g., 1,3-dibromo-2,2-dimethoxypropane) with the compound of Formula (2B) (e.g., tert-butyl 2-cyanoacetate) is performed at a temperature of about 150° C. In some embodiments, the reaction of the compound of Formula (2A) (e.g., 1,3-dibromo-2,2-dimethoxypropane) with the compound of Formula (2B) (e.g., tert-butyl 2-cyanoacetate) is performed at a temperature of about 160° C. It is understood that each description of the temperature may be combined with each description of $X^1$, $X^2$, R, the base and/or the organic solvent the same as if each and every combination were specifically and individually listed. For example, in some embodiments, the compound of Formula (2A) is 1,3-dibromo-2,2-dimethoxypropane; the compound of Formula (2B) is tert-butyl 2-cyanoacetate; the base is potassium tert-butoxide; the base is DMI; and the reaction of the 1,3-dibromo-2,2-dimethoxypropane and the tert-butyl 2-cyanoacetate is performed at a temperature of about 150° C.

In some embodiments, the compound of Formula (2A) (e.g., 1,3-dibromo-2,2-dimethoxypropane), the compound of Formula (2B) (e.g., tert-butyl 2-cyanoacetate), and the base are sequentially added to the organic solvent. In some embodiments, the compound of Formula (2A) (e.g., 1,3-dibromo-2,2-dimethoxypropane), the base, and the compound of Formula (2B) (e.g., tert-butyl 2-cyanoacetate) are sequentially added to the organic solvent. In some embodiments, the compound of Formula (2B) (e.g., tert-butyl 2-cyanoacetate), the compound of Formula (2A) (e.g., 1,3-dibromo-2,2-dimethoxypropane), and the base are sequentially added to the organic solvent. In some embodiments, the compound of Formula (2B) (e.g., tert-butyl 2-cyanoacetate), the base, and the compound of Formula (2A) (e.g., 1,3-dibromo-2,2-dimethoxypropane) are sequentially added to the organic solvent. In some embodiments, the base, the compound of Formula (2A) (e.g., 1,3-dibromo-2,2-dimethoxypropane), and the compound of Formula (2B) (e.g., tert-butyl 2-cyanoacetate) are sequentially added to the organic solvent. In some embodiments, the base, the compound of Formula (2B) (e.g., tert-butyl 2-cyanoacetate), and the compound of Formula (2A) (e.g., 1,3-dibromo-2,2-dimethoxypropane) are sequentially added to the organic solvent. In some embodiments, the compound of Formula (2A) (e.g., 1,3-dibromo-2,2-dimethoxypropane), the compound of Formula (2B) (e.g., tert-butyl 2-cyanoacetate), and the base are simultaneously added to the organic solvent.

In some embodiments, the product of the reaction of the compound of Formula (2A) (e.g., 1,3-dibromo-2,2-dimethoxypropane) with the compound of Formula (2B) (e.g., tert-butyl 2-cyanoacetate) is distilled before it is used in step (i).

In some embodiments, the method of preparing the compound of Formula (1) or a salt thereof further comprises obtaining the compound of Formula (1A) by converting a compound of Formula (1D):

(1D)

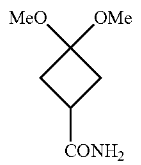

to the compound of Formula (1A). In some embodiments, the conversion of the compound of Formula (1D) to the compound of Formula (1A) is conducted in Toluene. In some embodiments, the conversion of the compound of Formula (1D) to the compound of Formula (1A) is conducted in the presence of TEA. In some embodiments, the conversion of the compound of Formula (1D) to the compound of Formula (1A) is conducted in the presence of TFAA. In some embodiments, the conversion of the compound of Formula (1D) to the compound of Formula (1A) is conducted at a temperature of about 0° C.

In some embodiments, the method further comprises obtaining the compound of Formula (1D) by converting a compound of Formula (1E):

(1E)

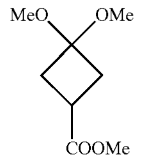

to the compound of Formula (1D). In some embodiments, the conversion of the compound of Formula (1E) to the compound of Formula (1D) is conducted in methanol. In some embodiments, the conversion of the compound of Formula (1E) to the compound of Formula (1D) is conducted in the presence of ammonia. In some embodiments, the conversion of the compound of Formula (1E) to the compound of Formula (1D) is conducted at a temperature at about 40° C.

In some embodiments, the method further comprises obtaining the compound of Formula (1E) by converting a compound of Formula (1F):

(1F)

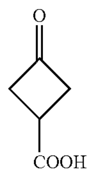

to the compound of Formula (1E). In some embodiments, the conversion of the compound of Formula (1F) to the compound of Formula (1E) is conducted in methanol. In some embodiments, the conversion of the compound of Formula (1F) to the compound of Formula (1E) is conducted in the presence of Amberlyst-15. In some embodiments, the conversion of the compound of Formula (1F) to the compound of Formula (1E) is conducted in the presence of trimethoxymethane. In some embodiments, the conversion of the compound of Formula (1F) to the compound of Formula (1E) is conducted at a temperature of about 55° C.

In another aspect, provided herein is a compound of Formula (1B):

(1B)

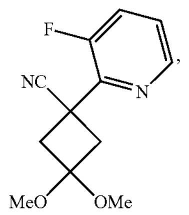

or a salt thereof.

In another aspect, provided herein is a method of preparing the compound of Formula (1B) or a salt thereof, wherein the method is as described herein.

In another aspect, provided herein is a compound of Formula (1D):

(1D)

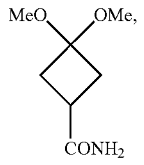

or a salt thereof.

In another aspect, provided herein is a method of preparing the compound of Formula (1D) or a salt thereof, wherein the method is as described herein.

Synthetic Schemes

Certain processes provided herein are described in reference to the illustrative synthetic schemes shown below and the specific examples that follow. Certain reactions and conversions described herein can be conducted using methods known in the art. For example, U.S. Pat. No. 8,962,632, WO 2011/133920, WO 2011/133888, and WO 2011/133882 describe methods and reagents that can be used to synthesize certain compounds disclosed herein. Skilled artisans will recognize that, to obtain various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Abbreviations used herein are explained in the following table.

Abbreviations

| Abbreviation | Meaning |
|---|---|
| DIPEA | N,N-diisopropyl-N-ethylamine |
| DMF | N,N-dimethylformamide |
| tBuOK | potassium tert-butoxide |
| DMI | 1,3-dimethyl-2-imidazolidinone |
| NaHMDS | sodium bis(trimethylsilyl)amide |
| $HC(OMe)_3$ | trimethyl orthoformate |
| MeOH | methanol |
| Me | methyl |
| $Et_3N$ | triethylamine |
| NMP | N-methylpyrrolidone |
| $Boc_2O$ | di-tert-butyl dicarbonate |
| DMAP | 4-dimethylaminopyridine |
| THF | tetrahydrofuran |
| TFA | trifluoroacetic acid |
| $Ac_2O$ | acetic anhydride |
| NaOMe | sodium methoxide |
| DMSO | dimethyl sulfoxide |
| Tos-Cl | 4-toluenesulfonyl chloride |
| DAST | diethylaminosulfur trifluoride |
| rt | room temperature |
| sat. | saturated |
| EtOAc | ethyl acetate |
| MTBE | methyl tert-butyl ether |
| TFAA | trifluoroacetic anhydride |
| TEA | triethanolamine |
| PE | petroleum ether |
| DCM | dichloromethane |

Scheme 1

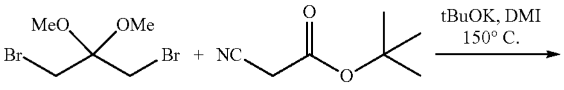

-continued

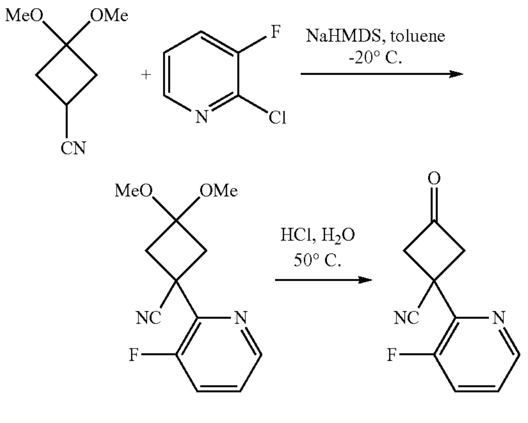

Scheme 1 illustrates a scheme of synthesizing the compound of Formula (1C).

Scheme 2

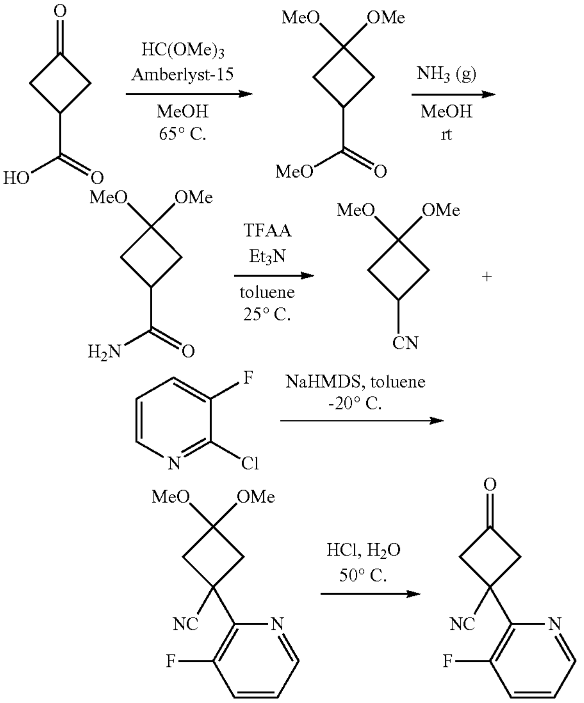

Scheme 2 illustrates an alternative scheme of synthesizing the compound of Formula (1C).

Scheme 3

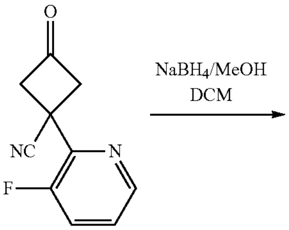

-continued

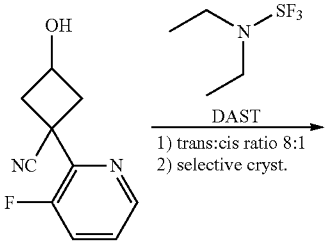

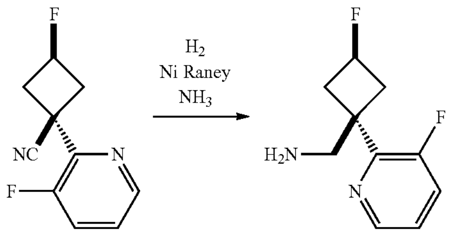

Scheme 3 illustrates a scheme of converting the compound of Formula (1C) to the compound of Formula (1I).

Scheme 4

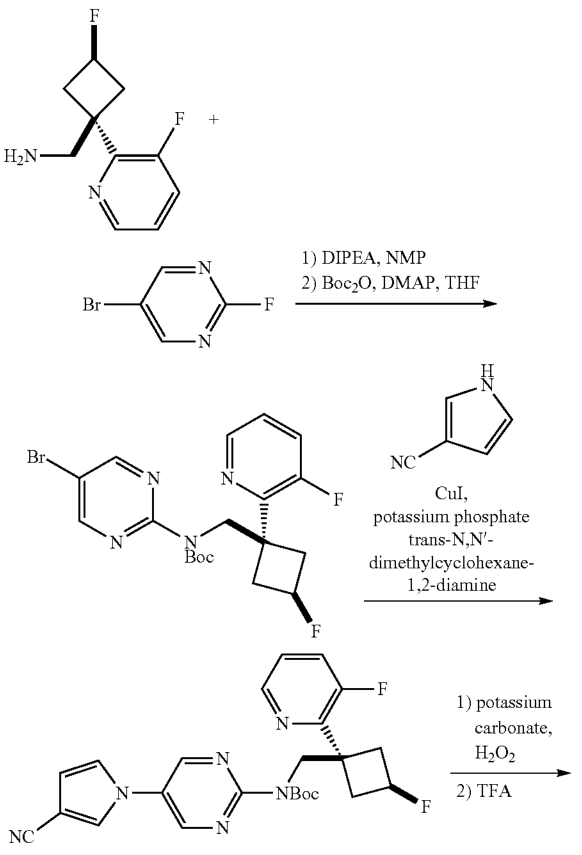

-continued

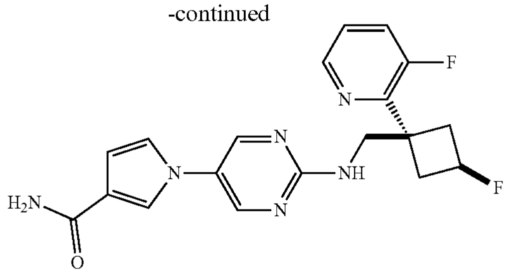

Scheme 4 illustrates a scheme of converting the compound of Formula (1I) to the compound of Formula (1).

EXAMPLES

Example 1. Synthesis of 3,3-dimethoxycyclobutane-1-carbonitrile

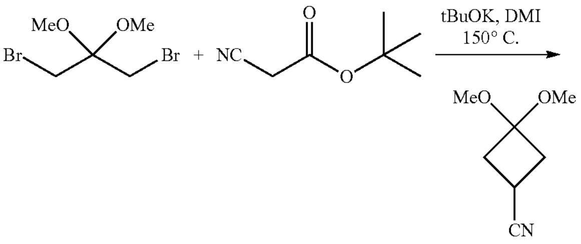

To a flask was added N-methylpyrrolidone (30 mL), tert-butyl cyanoacetate (8.08 g) at room temperature. To a resulting solution was added potassium tert-butoxide (7.71 g), 1,3-dibromo-2,2-dimethoxy propane (5.00 g) at 0° C. To another flask, potassium iodide (158 mg), 2,6-di-tert-butyl-p-cresol (42 mg), N-methylpyrrolidone (25 mL) were added at room temperature and then resulting solution was heated to 165° C. To this solution, previously prepared mixture was added dropwise at 140~165° C., then stirred for 2 hours at 165° C. To the reaction mixture, water (65 mL) was added. A resulting solution was extracted with toluene (40 mL, three times) and then combined organic layer was washed with water (20 mL, three times) and 1N NaOH aq. (20 mL). A resulting organic layer was concentrated below 50° C. under reduced pressure to give 3,3-dimethoxycyclobutane-1-carbonitrile (66% yield, GC assay) as toluene solution. $^1H$ NMR ($CDCl_3$, 400 MHz) δ 3.17 (s, 3H), 3.15 (s, 3H), 2.93-2.84 (m, 1H), 2.63-2.57 (m, 2H), 2.52-2.45 (m, 2H).

Example 2 Synthesis of methyl 3,3-dimethoxycyclobutane-1-carboxylate

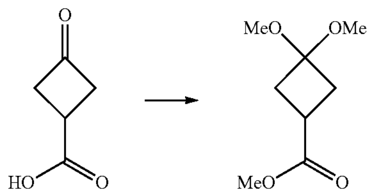 [SMILES: O=C1CC(C(=O)O)C1 ; COC(=O)C1CC(OC)(OC)C1]

A reactor was vacuumed to 0.02 MPa and less and then inerted with nitrogen to atmosphere for three times. MeOH (339.00 kg), 3-oxocyclobutanecarboxylic acid (85.19 kg, 746.6 mol, 1.0 eq.), Amberlyst-15 ion exchange resin (8.90 kg, 10% w/w), and trimethoxymethane (196.00 kg, 1847.3 mol, 2.5 eq.) were charged into the reactor and the resulting mixture was heated to 55±5° C. and reacted for 6 hours to give methyl 3,3-dimethoxycyclobutane-1-carboxylate solution in MeOH. $^1$H NMR ($CDCl_3$, 400 MHz) δ 3.70 (s, 3H), 3.17 (s, 3H), 3.15 (s, 3H), 2.94-2.85 (m, 1H), 2.47-2.36 (m, 4H).

Example 3 Synthesis of 3,3-dimethoxycyclobutane-1-carboxamide

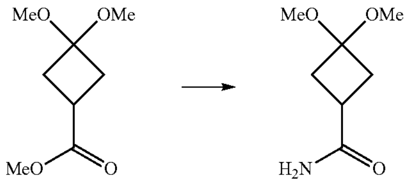 [SMILES: COC(=O)C1CC(OC)(OC)C1 ; COC1(OC)CC(C(N)=O)C1]

The methyl 3,3-dimethoxycyclobutane-1-carboxylate solution in MeOH prepared as described in Example 2 was cooled to below 25° C. and centrifuged. The filter cake was washed with MeOH (7.00 kg) and the filtrate was pumped to the reactor. The solution was concentrated under vacuum below 55° C. until the system had no more than 2 volumes. MeOH (139.40 kg) was charged to the reactor and the solution was concentrated under vacuum below 55° C. until the system had no more than 2 volumes. MeOH (130.00 kg) was charged to the reactor and the solution was concentrated under vacuum below 55° C. until the system had no more than 2 volumes. Half of the resulting solution was diluted with MeOH (435.00 kg) and cooled to below 30° C. $NH_3$ gas (133.80 kg) was injected into the reactor below 35° C. for 24 hours. The mixture was stirred at 40±5° C. for 72 hours. The resulting solution was concentrated under vacuum below 50° C. until the system had no more than 2 volumes. MTBE (181.00 kg) was charged into the reactor. The resulting solution was concentrated under vacuum below 50° C. until the system had no more than 2 volumes. PE (318.00 kg) was charged into the reactor. The resulting mixture was cooled to 5±5° C., stirred for 4 hours at 5±5° C., and centrifuged. The filter cake was washed with PE (42.00 kg) and the wet filter cake was put into a vacuum oven. The filter cake was dried at 30±5° C. for at least 8 hours to give 3,3-dimethoxycyclobutane-1-carboxamide as off-white solid (112.63 kg, 94.7% yield). $^1$H NMR ($CDCl_3$, 400 MHz) δ 5.76 (bs, 1H), 5.64 (bs, 1H), 3.18 (s, 3H), 3.17 (s, 3H), 2.84-2.76 (m, 1H), 2.45-2.38 (m, 4H).

Example 4 Synthesis of 3,3-dimethoxycyclobutane-1-carbonitrile

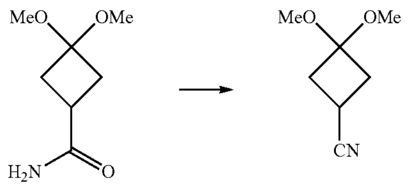 [SMILES: COC1(OC)CC(C(N)=O)C1 ; COC1(OC)CC(C#N)C1]

A reactor was vacuumed to 0.02 MPa and less and then inerted with nitrogen to atmosphere for three times. Toluene (500.00 kg), 3,3-dimethoxycyclobutane-1-carboxamide (112.54 kg, 706.9 mol, 1.0 eq.), and TEA (158.00 kg, 1561.3 mol, 2.20 eq) were charged into the reactor and the resulting mixture was cooled to 0±5° C. TFAA (164.00 kg, 781 mol, 1.10 eq.) was added dropwise at 0±5° C. The resulting mixture was stirred for 10 hours at 20±5° C. and cooled below 5±5° C. $H_2O$ (110.00 kg) was charged into the reactor at below 15° C. The resulting mixture was stirred for 30 minutes and the water phase was separated. The aqueous phase was extracted with toluene (190.00 kg) twice. The organic phases were combined and washed with $H_2O$ (111.00 kg). $H_2O$ was removed by azeotrope until the water content was no more than 0.03%. The resulting solution was cooled to below 20° C. to give 3,3-dimethoxycyclobutane-1-carbonitrile solution in toluene (492.00 kg with 17.83% assay content, 87.9% yield).

Example 5 Synthesis of 1-(3-fluoropyridin-2-yl)-3,3-dimethoxycyclobutane-1-carbonitrile

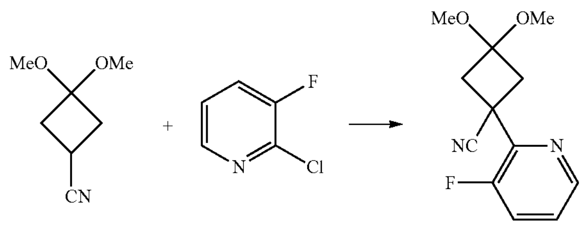 [SMILES: COC1(OC)CC(C#N)C1 ; Fc1cccnc1Cl ; COC1(OC)CC(C#N)(c2ncccc2F)C1]

A reactor was vacuumed to 0.02 MPa and less and then inerted with nitrogen to atmosphere for three times. The 3,3-dimethoxycyclobutane-1-carbonitrile solution in toluene prepared as described in Example 4 (246.00 kg of a 17.8% solution of 3,3-dimethoxycyclobutane-1-carbonitrile in toluene, 1.05 eq.) and 2-chloro-3-fluoropyridine (39.17 kg, 297.9 mol, 1.00 eq.) were charged into the reactor. The reactor was vacuumed to 0.02 MPa and less and then inerted with nitrogen to atmosphere for three times. The mixture was slowly cooled to −20±5° C. NaHDMS (2M in THF) (165.71 kg, 1.20 eq) was added dropwise at −20±5° C. The resulting mixture was stirred at −15±5° C. for 1 hour. The mixture was stirred until the content of 2-chloro-3-fluoropyridine is no more than 2% as measured by HPLC. Soft water (16.00 kg) was added dropwise at below 0° C. while maintaining the reactor temperature. The resulting solution was transferred to another reactor. Aq. $NH_4Cl$ (10% w/w, 88.60 Kg) was added dropwise at below 0° C. while maintaining the reactor temperature. Soft water (112.00 kg) was charged into the reactor and the aqueous phase was separated and collected. The aqueous phase was extracted with ethyl acetate (70.00 kg) and an organic phase was collected. The organic phase was washed with sat. NaCl (106.00 kg) and collected. The above steps were repeated to obtain another batch of organic phase. The two batches of organic phase were concentrated under vacuum below 70° C. until the system had no more than 2 volumes. The resulting solution was cooled to below 30° C. to give a 1-(3-fluoropyridin-2-yl)-3,3-dimethoxycyclobutane-1-carbonitrile solution. $^1$H NMR ($CDCl_3$, 400 MHz) δ 8.42-8.38 (m, 1H), 7.50-7.45 (m, 1H), 7.38-7.33 (m, 1H), 3.28 (s, 3H), 3.13 (s, 3H), 3.09-3.05 (m, 4H).

Example 6 Synthesis of 1-(3-fluoropyridin-2-yl)-3-oxocyclobutanecarbonitrile

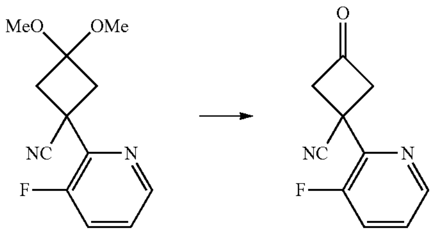 [SMILES: COC1(OC)CC(C#N)(c2ncccc2F)C1 ; N#CC1(c2ncccc2F)CC(=O)C1]

A reactor was vacuumed to 0.02 MPa and less and then inerted with nitrogen to atmosphere for three times. Water (603.00 kg) was added to the reactor and was stirred. Concentrated HCl (157.30 kg) was charged into the reactor at below 35° C. The 1-(3-fluoropyridin-2-yl)-3,3-dimethoxycyclobutane-1-carbonitrile solution prepared as described in Example 5 (206.00 kg) was charged into the reactor and the resulting mixture was heated to 50±5° C. and reacted for 3 hours at 50±5° C. The mixture was reacted until the content of 1-(3-fluoropyridin-2-yl)-3,3-dimethoxycyclobutane-1-carbonitrile was no more than 2.0% as measured by HPLC. The reaction mixture was cooled to below 30° C. and extracted with ethyl acetate (771.00 kg). An aqueous phase was collected and extracted with ethyl acetate (770.00 kg). The organic phases were combined and the combined organic phase was washed with soft water (290.00 kg) and brine (385.30 kg). The organic phase was concentrated under vacuum at below 60° C. until the system had no more than 2 volumes. Propan-2-ol (218.00 kg) was charged into the reactor. The organic phase was concentrated under vacuum at below 60° C. until the system had no more than 1 volume. PE (191.00 kg) was charged into the reactor at 40±5° C. and the resulting mixture was heated to 60±5° C. and stirred for 1 hour at 60±5° C. The mixture was then slowly cooled to 5±5° C. and stirred for 5 hours at 5±5° C. The mixture was centrifuged and the filter cake was washed with PE (48.00 kg) and the wet filter cake was collected. Water (80.00 kg), concentrated HCl (2.20 kg), propan-2-ol (65.00 kg), and the wet filter cake were charged in this order into a drum. The resulting mixture was stirred for 10 minutes at 20±5° C. The mixture was centrifuged and the filter cake was washed with a mixture solution containing 18.00 kg of propan-2-ol, 22.50 kg of soft water, and 0.60 kg of concentrated HCl. The filter cake was put into a vacuum oven and dried at 30±5° C. for at least 10 hours. The filter cake was dried until the weight did not change to give 1-(3-fluoropyridin-2-yl)-3-oxocyclobutanecarbonitrile as off-white solid (77.15 kg, 68.0% yield). $^1H$ NMR ($CDCl_3$, 400 MHz) δ 8.45-8.42 (m, 1H), 7.60-7.54 (m, 1H), 7.47-7.41 (m, 1H), 4.18-4.09 (m, 2H), 4.02-3.94 (m, 2H).

Example 7 Synthesis of 1-(3-fluoropyridin-2-yl)-3-hydroxycyclobutanecarbonitrile

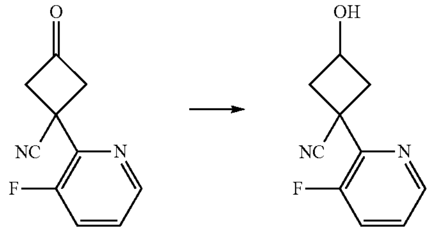 [SMILES: N#CC1(c2ncccc2F)CC(=O)C1 ; N#CC1(c2ncccc2F)CC(O)C1]

To a solution of 1-(3-fluoropyridin-2-yl)-3-oxocyclobutanecarbonitrile (231 g, 1.22 mol) in a mixture of DCM (2 L) and MeOH (200 mL) was added $NaBH_4$ portionwise at −78° C. The reaction mixture was stirred at −78° C. for 1 hour and quenched with a mixture of methanol and water (1:1). The organic layer was washed with water (500 mL×3), dried over $Na_2SO_4$, and concentrated. The residue was purified on silica gel (50% EtOAc/hexanes) to provide the title compound as an amber oil (185.8 g, 77.5%). Low Resolution Mass Spectrometry (LRMS) (M+H) m/z 193.2.

Example 8 Synthesis of (1s,3s)-3-fluoro-1-(3-fluoropyridin-2-yl)cyclobutane-1-carbonitrile

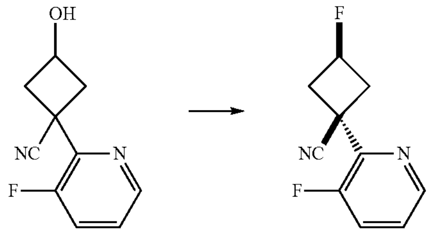 [SMILES: N#CC1(c2ncccc2F)CC(O)C1 ; N#C[C@]1(c2ncccc2F)C[C@H](F)C1]

To a solution of 1-(3-fluoropyridin-2-yl)-3-hydroxycyclobutanecarbonitrile (185 g, 0.96 mol) in DCM (1 L) was added DAST portionwise at 0-10° C. Upon the completion of addition, the reaction was refluxed for 6 hours. The reaction was cooled to rt and poured onto sat. $NaHCO_3$ solution. The mixture was separated and the organic layer was washed with water, dried over $Na_2SO_4$, and concentrated. The residue was purified on silica gel (100% DCM) to provide the title compound as a brown oil (116 g) in a 8:1 trans:cis mixture. The above brown oil (107 g) was dissolved in toluene (110 mL) and hexanes (330 mL) at 70° C. The solution was cooled to 0° C. and stirred at 0° C. overnight. The precipitate was filtered and washed with hexanes to provide the trans isomer as a white solid (87.3 g). LRMS (M+H) m/z 195.1.

Example 9 Synthesis of ((1r,3r)-3-fluoro-1-(3-fluoropyridin-2-yl)cyclobutyl)methanamine

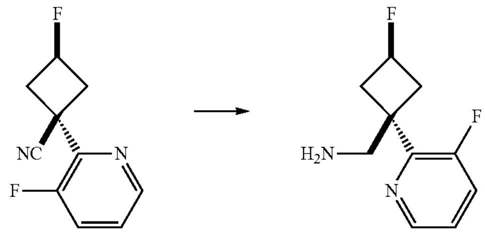 [SMILES: N#C[C@]1(c2ncccc2F)C[C@H](F)C1 ; NC[C@]1(c2ncccc2F)C[C@H](F)C1]

A mixture of (1s,3s)-3-fluoro-1-(3-fluoropyridin-2-yl)cyclobutane-1-carbonitrile (71 g, 0.37 mol) and Raney nickel (~7 g) in 7N ammonia in methanol (700 mL) was charged with hydrogen (60 psi) for 2 days. The reaction was filtered through a celite pad and washed with methanol. The filtrate was concentrated under high vacuum to provide the title compound as a light green oil (70 g, 97.6%). LRMS (M+H) m/z 199.2.

Example 10 Synthesis of t-butyl 5-bromopyrimidin-2-yl((trans-3-fluoro-1-(3-fluoropyridin-2-yl)cyclobutyl)methyl)carbamate

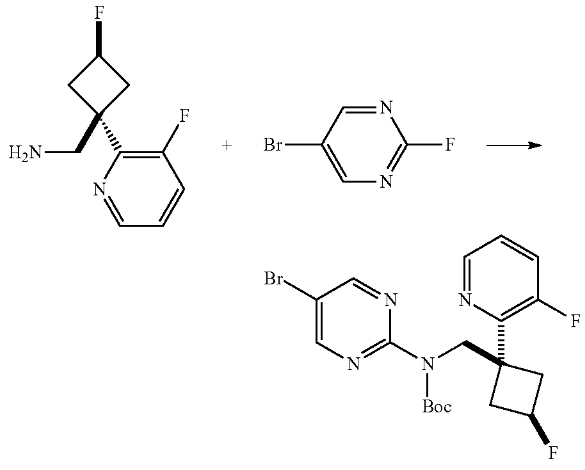

A mixture of ((1r,3r)-3-fluoro-1-(3-fluoropyridin-2-yl)cyclobutyl)methanamine (37.6 g, 190 mmol), 5-bromo-2-fluoropyrimidine (32.0 g, 181 mmol), DIPEA (71 mL, 407 mmol), and NMP (200 mL) was stirred at rt overnight. The reaction mixture was then diluted with EtOAc (1500 mL) and washed with saturated sodium bicarbonate (500 mL). The organic layer was separated, dried over $Na_2SO_4$, and concentrated. The resultant solid was dissolved in THF (600 mL), followed by the slow addition of DMAP (14 g, 90 mmol) and $Boc_2O$ (117.3 g, 542 mmol). The reaction was heated to 60° C. and stirred for 3 h. The reaction mixture was then concentrated and purified by silica gel chromatography (EtOAc/hex) to give 59.7 g of t-butyl 5-bromopyrimidin-2-yl((trans-3-fluoro-1-(3-fluoropyridin-2-yl)cyclobutyl)methyl)carbamate as a white solid.

Example 11 Synthesis of t-butyl 5-(3-cyano-1H-pyrrol-1-yl)pyrimidin-2-yl(((trans)-3-fluoro-1-(3-fluoropyridin-2-yl)cyclobutyl)methyl)carbamate

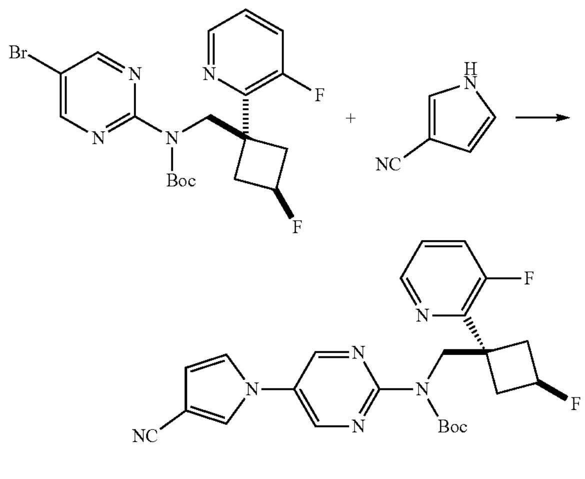

To a solution of t-butyl 5-bromopyrimidin-2-yl((trans-3-fluoro-1-(3-fluoropyridin-2-yl)cyclobutyl)methyl) carbamate (1.0 g, 2.8 mmol) in 15 mL of toluene (degassed with nitrogen) was added copper iodide (100 mg, 0.6 mmol), potassium phosphate (1.31 g, 6.2 mmol), trans-N,N'-dimethylcyclohexane-1,2-diamine (320 mg, 2.2 mmol), and 3-cyanopyrrole (310 mg, 3.6 mmol). The reaction was heated to 100° C. and stirred for 2 h. The reaction was then concentrated and purified by silica gel chromatography (EtOAc/hexanes) to afford 1.1 g of t-butyl 5-(3-cyano-1H-pyrrol-1-yl)pyrimidin-2-yl(((trans)-3-fluoro-1-(3-fluoropyridin-2-yl)cyclobutyl)methyl)carbamate as a clear oil.

Example 12 Synthesis of 1-(2-((((trans)-3-fluoro-1-(3-fluoropyridin-2-yl)cyclobutyl)methyl)amino)pyrimidin-5-yl)-1H-pyrrole-3-carboxamide

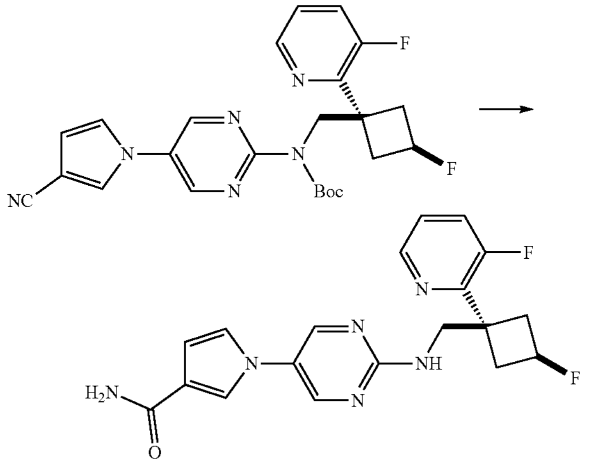

To a solution of t-butyl 5-(3-cyano-1H-pyrrol-1-yl)pyrimidin-2-yl(((trans)-3-fluoro-1-(3-fluoropyridin-2-yl)cyclobutyl)methyl)carbamate (1.1 g, 3.1 mmol) in DMSO (10 mL) was added potassium carbonate (1.3 g, 9.3 mmol). The mixture was cooled to 0° C. and hydrogen peroxide (3 mL) was slowly added. The reaction was warmed to rt and stirred for 90 min. The reaction was diluted with EtOAc (75 mL) and washed three times with brine (50 mL). The organic layer was then dried over $Na_2SO_4$, filtered, and concentrated to give a crude solid that was purified by silica gel chromatography (10% $MeOH/CH_2Cl_2$) to afford 1.07 g of a white solid compound. This compound was dissolved in 25% $TFA/CH_2Cl_2$ and stirred for 1 hour. The reaction was then concentrated, dissolved in ethyl acetate (75 mL), and washed three times with saturated potassium carbonate solution. The organic layer was then dried over $Na_2SO_4$, filtered, and concentrated to give a crude solid that was triturated with 75% ethyl acetate/hexanes. The resultant slurry was sonicated and filtered to give 500 mg of 1-(2-((((trans)-3-fluoro-1-(3-fluoropyridin-2-yl)cyclobutyl) methyl)amino)pyrimidin-5-yl)-1H-pyrrole-3-carboxamide as a white solid. LRMS (M+H=385).

While the foregoing written description of the methods, compounds, and compositions described herein enables one of ordinary skill to make and use the methods, compounds, and compositions described herein, those of ordinary skill will understand and appreciate the existence of variations, combinations, and equivalents of the specific embodiment, method, schemes, and examples herein. The methods, compounds, and compositions provided herein should therefore not be limited by the above-described embodiments, methods, schemes, or examples, but rather encompasses all embodiments and methods within the scope and spirit of the methods, compounds, and compositions provided herein.

Each reference disclosed herein is incorporated by reference in its entirety.

The invention claimed is:

1. A method of preparing a compound of Formula (1):

(1)

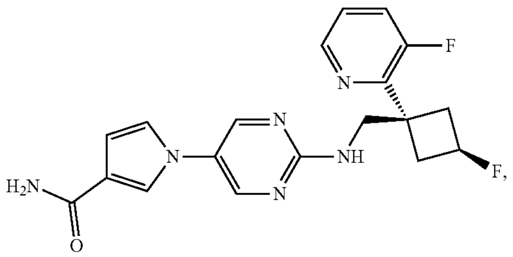

or a salt thereof, comprising:

(i) reacting a compound of Formula (1A):

(1A)

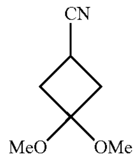

with 2-chloro-3-fluoropyridine to form a compound of Formula (1B):

(1B)

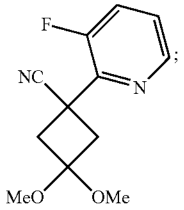

(ii) reacting the compound of Formula (1B) with an aqueous acid to form a compound of Formula (1C):

(1C)

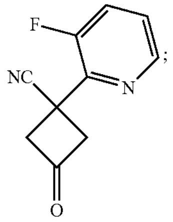

and (iii) converting the compound of Formula (1C) to the compound of Formula (1) or a salt thereof.

2. The method of claim 1, further comprising obtaining the compound of Formula (1A) by reacting 1,3-dibromo-2,2-dimethoxypropane with tert-butyl 2-cyanoacetate to form the compound of Formula (1A).

3. The method of claim 2, wherein the reaction of the 1,3-dibromo-2,2-dimethoxypropane with the tert-butyl 2-cyanoacetate is performed in the presence of a base.

4. The method of claim 3, wherein the base is potassium tert-butoxide.

5. The method of claim 1, further comprising obtaining the compound of Formula (1A) by converting a compound of Formula (1D):

(1D)

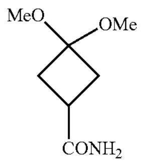

to the compound of Formula (1A).

6. The method of claim 5, further comprising obtaining the compound of Formula (1D) by converting a compound of Formula (1E):

(1E)

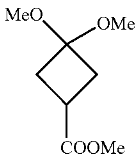

to the compound of Formula (1D).

7. The method of claim 6, further comprising obtaining the compound of Formula (1E) by converting a compound of Formula (1F):

(1F)

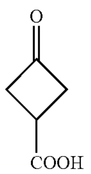

to the compound of Formula (1E).

8. The method of claim 1, wherein step (i) is performed in the presence of a base.

9. The method of claim 8, wherein the base is sodium bis(trimethylsilyl)amide.

10. The method of claim 1, wherein the aqueous acid of step (ii) is aqueous hydrochloric acid.

11. The method of claim 1, wherein step (iii) comprises converting the compound of Formula (1C) to a compound of Formula (1G):

(1G)

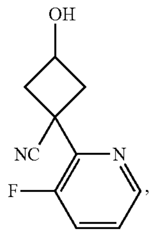

and converting the compound of Formula (1G) to the compound of Formula (1) or a salt thereof.

12. The method of claim 11, wherein step (iii) further comprises converting the compound of Formula (1G) to a compound of Formula (1H):

(1H)

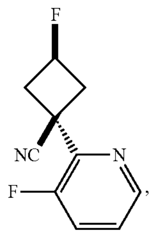

and converting the compound of Formula (1H) to the compound of Formula (1) or a salt thereof.

13. The method of claim 12, wherein step (iii) further comprises converting the compound of Formula (1H) to a compound of Formula (1I)

(1I)

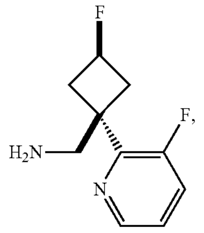

and converting the compound of Formula (1I) to the compound of Formula (1) or a salt thereof.

14. The method of claim 13, wherein step (iii) further comprises reacting the compound of Formula (1I) with

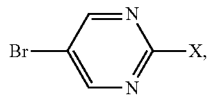

wherein X is chloro or fluoro, to form a compound of Formula (1J):

(1J)

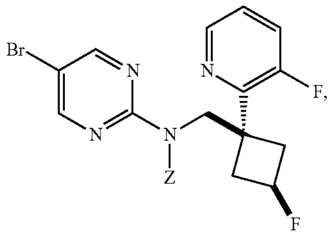

wherein Z is a protecting group or hydrogen, and converting the compound of Formula (1J) to the compound of Formula (1) or a salt thereof.

15. The method of claim 14, wherein step (iii) further comprises reacting the compound of Formula (1J) with

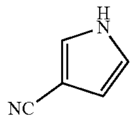

to form a compound of Formula (1K):

(1K)

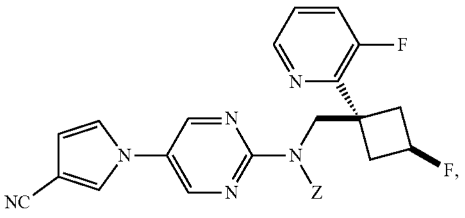

wherein Z is a protecting group or hydrogen, and converting the compound of Formula (1K) to the compound of Formula (1) or a salt thereof.

16. The method of claim 15, wherein step (iii) further comprises isolating the compound of Formula (1) or a salt thereof.

17. A compound of Formula (1B):

(1B)

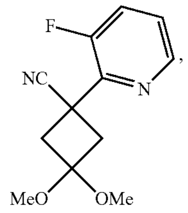

or a salt thereof.

18. A method of preparing a compound of Formula (1B):

(1B)

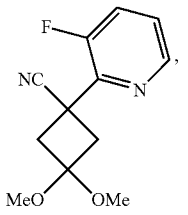

or a salt thereof, comprising:

reacting a compound of Formula (1A):

(1A)

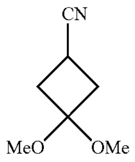

with 2-chloro-3-fluoropyridine to form the compound of Formula (1B).

19. The method of claim 18, further comprising obtaining the compound of Formula (1A) by reacting 1,3-dibromo-2,2-dimethoxypropane with tert-butyl 2-cyanoacetate to form the compound of Formula (1A).

20. The method of claim 19, wherein the reaction of the 1,3-dibromo-2,2-dimethoxypropane with the tert-butyl 2-cyanoacetate is performed in the presence of a base.

21. The method of claim 20, wherein the base is potassium tert-butoxide.

22. The method of claim 18, further comprising obtaining the compound of Formula (1A) by converting a compound of Formula (1D):

(1D)

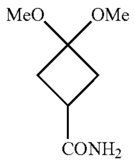

to the compound of Formula (1A).

23. The method of claim 22, further comprising obtaining the compound of Formula (1D) by converting a compound of Formula (1E):

(1E)

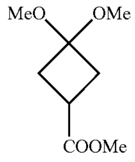

to the compound of Formula (1D).

24. The method of claim 23, further comprising obtaining the compound of Formula (1E) by converting a compound of Formula (1F):

(1F)

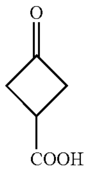

to the compound of Formula (1E).

25. The method of claim 18, wherein the reaction of the compound of Formula (1A) with the 2-chloro-3-fluoropyridine is performed in the presence of a base.

26. The method of claim 25, wherein the base is sodium bis(trimethylsilyl)amide.

27. A compound of Formula (1D):

(1D)

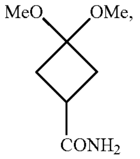

or a salt thereof.

28. A method of preparing a compound of Formula (1D):

(1D)

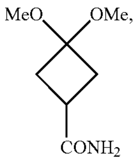

or a salt thereof, comprising converting a compound of Formula (1E):

(1E)

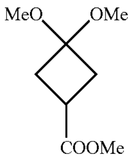

to the compound of Formula (1D) or a salt thereof.

29. The method of claim 28, further comprising obtaining the compound of Formula (1E) by converting a compound of Formula (1F):

(1F)

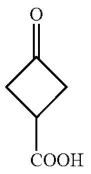

to the compound of Formula (1E).

* * * * *